United States Patent [19]
Bornzin et al.

[11] Patent Number: 5,514,162
[45] Date of Patent: May 7, 1996

[54] SYSTEM AND METHOD FOR AUTOMATICALLY DETERMINING THE SLOPE OF A TRANSFER FUNCTION FOR A RATE-RESPONSIVE CARDIAC PACEMAKER

[75] Inventors: Gene A. Bornzin, Camarillo; Elia R. Arambula, Artesia; Joseph J. Florio, Sunland, all of Calif.

[73] Assignee: Pacesetter, Inc., Sylmar, Calif.

[21] Appl. No.: 255,194

[22] Filed: Jun. 7, 1994

[51] Int. Cl.$^6$ ............................................. A61N 1/36
[52] U.S. Cl. ............................................................ 607/19
[58] Field of Search ................................. 607/17–26, 30

[56] References Cited

U.S. PATENT DOCUMENTS

| 4,940,052 | 7/1990 | Mann et al. | 607/17 |
| 5,074,302 | 12/1991 | Poore et al. | 607/19 |
| 5,292,341 | 3/1994 | Snell | 607/30 |

FOREIGN PATENT DOCUMENTS

| 2213729 | 8/1989 | United Kingdom | 607/19 |

*Primary Examiner*—William E. Kamm
*Assistant Examiner*—Jeffrey R. Jastrzab
*Attorney, Agent, or Firm*—Lisa P. Weinberg

[57] ABSTRACT

A rate-responsive pacemaker measures a patient's level of activity and stores the results in an activity level histogram. The patient's average level of activity is maintained as a running average. Based on a prescribed base pacing rate, a prescribed maximum pacing rate, the average level of activity, and the measured levels of activity stored in the activity level histogram, the rate-responsive pacemaker automatically calculates the slope of the pacemaker transfer function. An activity deviation histogram is also maintained. Analysis of the activity deviation histogram allows the pacemaker to determine if the patient was usually inactive for an extended period of time, and to inhibit an automatic slope calculation under such conditions. If a patient desires to reach a prescribed target heart rate during exercise, the slope may be calculated using the target heart rate and a prescribed fraction of time each week that the patient devotes to exercise.

52 Claims, 7 Drawing Sheets

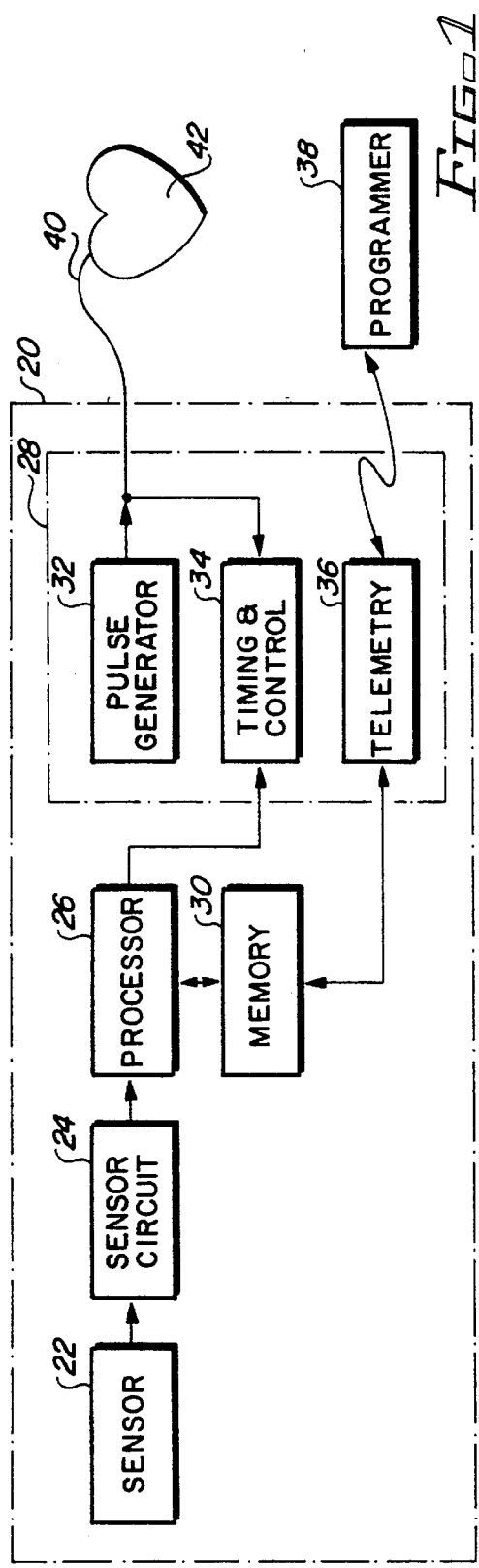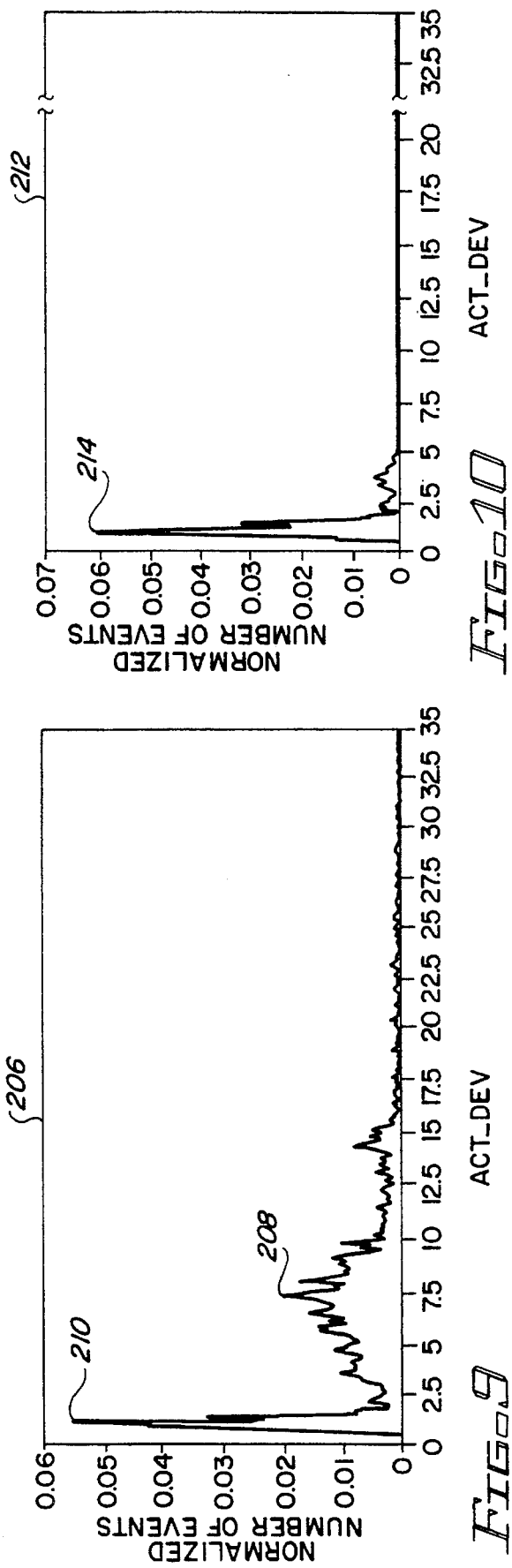

FIG. 11

| PROGRAMMED SLOPE | VERY FAST (SECS) | FAST (SECS) | MEDIUM (SECS) | SLOW (SECS) |
|---|---|---|---|---|
| 1 | 1*/10** (9.2) | 1/5 (17.6) | 1/3 (28.6) | 2/3 (35.2) |
| 2 | 1/7 (8.5) | 1/3 (19.3) | 1/2 (28.8) | 2/3 (38.5) |
| 3 | 1/3 (9.0) | 1/3 (18.6) | 2/3 (29.2) | 3/4 (33.6) |
| 4 | 1/4 (9.1) | 1/2 (17.4) | 3/4 (27.2) | 2/2 (34.7) |
| 5 | 1/3 (9.7) | 2/3 (19.4) | 1/1 (28.0) | 4/3 (38.7) |
| 6 | 1/3 (8.5) | 2/3 (17.0) | 2/2 (25.3) | 3/2 (37.9) |
| 7 | 1/2 (10.8) | 1/1 (20.9) | 3/2 (32.5) | 2/1 (41.8) |
| 8 | 1/2 (7.9) | 1/1 (17.9) | 3/2 (28.6) | 2/1 (33.8) |
| 9 | 1/2 (7.9) | 1/1 (15.2) | 2/1 (30.3) | 5/2 (39.4) |
| 10 | 1/1 (11.8) | 3/2 (18.9) | 2/1 (23.7) | 3/1 (35.5) |
| 11 | 1/1 (10.0) | 2/1 (20.0) | 3/1 (29.9) | 4/1 (39.9) |
| 12 | 1/1 (8.7) | 2/1 (17.5) | 3/1 (26.2) | 4/1 (34.9) |
| 13 | 1/1 (7.5) | 2/1 (15.0) | 4/1 (30.2) | 5/1 (37.7) |
| 14 | 1/1 (6.4) | 3/1 (19.0) | 4/1 (25.4) | 6/1 (38.1) |
| 15 | 1/1 (5.2) | 3/1 (15.5) | 5/1 (25.8) | 7/1 (36.0) |
| 16 | 2/1 (8.0) | 5/1 (19.9) | 7/1 (27.9) | 9/1 (35.8) |

FIG. 12

| PROGRAMMED SLOPE | FAST | MEDIUM | SLOW |
|---|---|---|---|
| 1 | 1 (1.4) | 3 (4.2) | 4 (5.7) |
| 2 | 2 (8.5) | 4 (3.8) | 5 (4.7) |
| 3 | 3 (9.0) | 5 (3.5) | 7 (4.9) |
| 4 | 4 (9.1) | 6 (3.6) | 9 (4.0) |
| 5 | 4 (1.9) | 8 (3.7) | 11 (5.1) |
| 6 | 5 (2.0) | 9 (3.6) | 12 (4.8) |
| 7 | 6 (1.1) | 10 (3.5) | 14 (4.9) |
| 8 | 7 (2.1) | 12 (3.6) | 17 (5.1) |
| 9 | 8 (2.0) | 16 (3.5) | 20 (5.0) |
| 10 | 10 (2.0) | 18 (3.6) | 25 (4.9) |
| 11 | 11 (2.0) | 21 (3.5) | 30 (5.0) |
| 12 | 14 (2.0) | 24 (3.5) | 34 (4.9) |
| 13 | 16 (2.0) | 28 (3.5) | 40 (5.0) |
| 14 | 19 (2.0) | 33 (3.5) | 47 (5.0) |
| 15 | 23 (2.0) | 41 (3.5) | 58 (5.0) |
| 16 | 30 (2.0) | 53 (3.5) | 70 (5.0) |

SYSTEM AND METHOD FOR AUTOMATICALLY DETERMINING THE SLOPE OF A TRANSFER FUNCTION FOR A RATE-RESPONSIVE CARDIAC PACEMAKER

BACKGROUND OF THE INVENTION

This invention relates to implantable cardiac pacemakers, and particularly to rate-responsive cardiac pacemakers. More particularly, this invention relates to a system and method for automatically determining the slope of a transfer function that is used by a rate-responsive pacemaker to determine an appropriate heart rate in accordance with metabolic demands.

A pacemaker is an implantable medical device which delivers electrical stimulation pulses to cardiac tissue to relieve symptoms associated with bradycardia—a condition in which a patient cannot normally maintain a physiologically acceptable heart rate. Early pacemakers delivered stimulation pulses at regular intervals in order to maintain a predetermined heart rate—typically a rate deemed to be appropriate for the patient at rest. The predetermined rate was usually set at the time the pacemaker was implanted, although in more advanced pacemakers, the rate could be set remotely after implantation. Such pacemakers were known as "asynchronous" pacemakers because they did not synchronize pacing pulses with natural cardiac activity.

Early advances in pacemaker technology included the ability to sense the patient's natural cardiac rhythm (i.e., the patient's intracardiac electrogram, or "IEGM"). This led to the development of "demand pacemakers"—so named because they deliver stimulation pulses only as needed by the heart. Demand pacemakers are capable of detecting a spontaneous, hemodynamically effective cardiac contraction which occurs within a predetermined time period (commonly referred to as the "escape interval") following a preceding contraction. When a naturally occurring contraction is detected within the escape interval, the demand pacemaker does not deliver a pacing pulse. The ability of demand pacemakers to avoid delivery of unnecessary stimulation pulses is desirable because pacing pulse inhibition extends battery life.

Demand pacemakers allow physicians to telemetrically adjust the length of the escape interval, which has the effect of altering the heart rate maintained by the device. However, in early devices, this flexibility only allowed for adjustments to a fixed programmed rate, and did not accommodate patients who required increased or decreased heart rates to meet changing physiological requirements during periods of elevated or reduced physical activity. Therefore, unlike a person with a properly functioning heart, a patient receiving therapy from an early demand pacemaker was paced at a constant heart rate—regardless of the level to which the patient was engaged in physical activity. Thus, during periods of elevated physical activity, the patient was subject to adverse physiological consequences, including lightheadedness and episodes of fainting, because the heart rate was forced by the pacemaker to remain constant.

The adverse effects of constant rate pacing lead to the development of "rate-responsive pacemakers" which can automatically adjust the patient's heart rate in accordance with metabolic demands. An implanted rate-responsive pacemaker typically operates to maintain a predetermined minimum heart rate when the patient is engaged in physical activity at or below a threshold level, and gradually increases the maintained heart rate in accordance with increases in physical activity until a maximum rate is reached. Rate-responsive pacemakers typically include processing circuitry that correlates measured physical activity to an appropriate heart rate. In many rate-responsive pacemakers, the minimum heart rate, maximum heart rate, and the transition rates between the minimum heart rate and the maximum heart rate are parameters that may be telemetrically adjusted to meet the needs of a particular patient.

One approach that has been considered for enabling rate-responsive pacemakers to determine an appropriate heart rate involves the use of a physiological parameter that reflects the patient's level of metabolic need. Physiological parameters that have been considered include central venous blood temperature, blood pH level, QT time interval and respiration rate. However, certain drawbacks (such as slow response time, unpredictable emotionally-induced variations, and wide variability across individuals) render the use of these physiological parameters difficult, and accordingly, they have not been widely used in practice.

Rather, most rate-responsive pacemakers employ sensors that transduce mechanical forces associated with physical activity, the level of physical activity being indicative of the patient's level of metabolic need. These activity sensors generally contain a piezoelectric transducing element which generates a measurable electrical potential when a mechanical stress resulting from physical activity is experienced by the sensor. By analyzing the signal from a piezoelectric activity sensor, a rate-responsive pacemaker can determine how frequently pacing pulses should be applied to the patient's heart.

Piezoelectric elements for activity sensors are commonly formed from piezoelectric crystals, such as quartz or barium titanite. Recently, however, activity sensors have been designed which use thin films of a piezoelectric polymer, such as polyvinylidene fluoride (commonly known by the trademark KYNAR, owned by ATOCHEM North America) as the transducing element, rather than the more commonly used piezoelectric crystals. Activity sensors so designed are described in copending, commonly-assigned U.S. patent applications Ser. No. 08/059,698, filed May 10, 1993, entitled "A Rate-Responsive Implantable Stimulation Device Having a Miniature Hybrid-Mountable Accelerometer-Based Sensor and Method of Fabrication," and Ser. No. 08/091,850, filed Jul. 14, 1993, entitled "Accelerometer-Based Multi-Axis Physical Activity Sensor for a Rate-Responsive Pacemaker and Method of Fabrication," which are hereby incorporated by reference in their entireties.

A variety of signal processing techniques have been used to process the raw sensor signals provided by activity sensors. For example, in one approach, the raw signals are rectified and filtered. Alternatively, the frequency at which the highest peaks in the signals occur can be monitored. Regardless of the particular method used, the result is typically a digital signal that is indicative of the level of sensed activity at a given time. In one preferred approach, the digital signal is produced by repeatedly integrating the raw sensor signals until a predetermined threshold value is reached. Each time the threshold is reached, a digital trigger pulse is generated. A counter is used to count the number of trigger pulses that occur in a fixed period of time (e.g., the number of trigger pulses that occur during an approximately 100 ms period within each heartbeat interval). The count reached at the end of the fixed period of time is provided to processing circuitry in the pacemaker, which processing circuitry typically includes a microprocessor.

The microprocessor then uses the count signal to produce a sensor level index signal that represents the patient's activity level. The appropriate rate at which the patient's heart is to be stimulated (known as the sensor-indicated rate) is determined by applying a transfer function to the sensor level index signal. The transfer function defines a sensor-indicated rate for each possible sensor level index signal.

An example of a rate-responsive pacemaker in which a transfer function is used to calculate the sensor-indicated rate is described in commonly-assigned U.S. Pat. No. 5,074,302 of Poore et al. ("the '302 patent"), which is hereby incorporated by reference in its entirety. As described therein, when relatively little activity is detected, the sensor level index signal is ordinarily below a low activity threshold. When the sensor level index signal is below the low activity threshold, the sensor-indicated rate is set to a base pacing rate (e.g., 60 beats per minute (bpm)), as defined by the transfer function. At high levels of measured activity, the sensor level index signal may exceed a high activity threshold. When this occurs, the sensor-indicated rate is limited to a maximum pacing rate, so that the patient's heart is not stimulated too rapidly. If the value of the sensor level index signal falls between the low and high activity thresholds, the pacemaker applies pacing pulses to the patient's heart in accordance with the rate determined by the transfer function, generally at a rate somewhere between the base pacing rate and the maximum pacing rate.

Typically, for sensor level index signals between the low and high thresholds, the transfer function is linear. The slope of the transfer function determines increases (or decreases) in the pacing rate corresponding to a given increase (or decrease) in the sensor level index signal. The larger the slope, the more dramatically the pacing rate will increase (or decrease) for a given sensor level.

The slope of the transfer function in typical rate-responsive pacemakers is telemetrically adjustable by a physician, so that the operation of a pacemaker can be tailored to suit an individual patient's needs. However, the task of manually selecting an appropriate slope for the transfer function is labor intensive and time consuming. Generally, the process of manually selecting the slope of the transfer function requires the patient to walk about for a period of time after each adjustment to the slope, so that the physician can monitor the performance of the pacemaker under each new slope setting.

In order to avoid the drawbacks associated with manual slope selection, pacemakers have been designed which can automatically adjust the slope of the transfer function, as described in the '302 patent. In order to automatically adjust the slope, the pacemaker described in the '302 patent measures the level of patient activity for a predetermined period of time. Because most patients are generally at rest for most of the day, the average of the sensor level index signals is approximately the same as the sensor level index signal for the patient at rest. Therefore, as described in the '302 patent, by calculating the average sensor level index signal over the predetermined period of time, a sensor level index signal can be generated that is appropriate to use as the low activity threshold. Similarly, a satisfactory determination of an appropriate value for the high activity threshold can be made by averaging some of the highest sensor level index signals that are measured during the same predetermined period of time. In this way, the pacemaker of the '302 patent is capable of automatically updating the low and high activity thresholds, which in turn has the effect of defining the slope of the transfer function.

Although the approach for adjusting the slope of the transfer function described in the '302 patent is generally satisfactory, it would be desirable if there were an approach for calculating and updating the slope of the transfer function that would allow a pacemaker to take into account certain aspects of a patient's condition that have previously not been addressed. For example, it would be desirable if the slope of the transfer function could be automatically determined based on the physician's selection of the base pacing rate and the maximum pacing rate, along with the patient's activity profile. It would also be desirable if the pacemaker could determine when the patient has been unusually inactive for an extended period of time, so that the pacemaker does not set an inappropriately steep slope for the transfer function. It would further be desirable if the pacemaker could set the slope of the transfer function in accordance with the patient's regular exercise routine.

SUMMARY OF THE INVENTION

In accordance with the present invention, a system and method for automatically determining the slope of a transfer function used by a rate-responsive cardiac pacemaker are provided. In a preferred embodiment, the pacemaker includes a conventional pacemaker circuit which is capable of generating pacing pulses in any of the known pacing modes in accordance with instructions provided by processing circuitry (which preferably includes a microprocessor). Pacing pulses are delivered to the patient's heart through at least one conventional pacing lead, which is also used to sense natural cardiac activity when pacing pulses are not being delivered. By sensing natural cardiac activity, the pacemaker is capable of operating in a demand mode, which advantageously extends battery life.

The processing circuitry regulates the operation of the pacemaker circuit in accordance with control routines and parameters that are stored in a memory. The control routines and parameters may be modified by a physician through the use of an external programmer, which communicates with the pacemaker through a telemetry circuit included within the pacemaker. In addition, the telemetry circuit may be used to communicate information from the pacemaker to the external programmer, such information including cardiac activity sensed by the pacing lead.

The rate-responsive pacemaker includes a sensor for measuring metabolic need, preferably an activity sensor that measures the patient's level of physical activity at a given time. Preferably, the activity sensor contains a piezoelectric element that generates a measurable electrical potential when a mechanical stress resulting from physical activity is experienced by the sensor. Suitable activity sensors are described in the above-incorporated U.S. patent application Ser. Nos. 08/059,698 and 08/091,850, although other types of activity sensors may be used.

The rate-responsive pacemaker also includes sensor circuitry for conditioning the raw sensor signals generated by the activity sensor. Preferably, the sensor circuitry provides digital sensor signals to the processing circuitry, which further processes the digital sensor signals to derive sensor level index signals. The sensor level index signals are used by the processing circuitry to determine the rate at which pacing pulses should be applied to the patient's heart.

The processing circuitry determines the appropriate pacing rate by using a transfer function. The transfer function is characterized by a base pacing rate (e.g., 60 bpm) for low activity levels and a maximum pacing rate (e.g., 150 bpm) for high activity levels. Preferably, both the base pacing rate and the maximum pacing rate are selected by the physician based on an assessment of the patient's condition. When the sensor level index signal derived by the processing circuitry is below a low activity threshold, the pacemaker circuit is instructed by the processing circuitry to generate pacing pulses at the base rate as needed by the patient's heart. When the sensor level index signal exceeds a high activity threshold, the pacemaker circuit is instructed to generate pacing pulses at the maximum pacing rate, as needed.

The rate at which the rate-responsive pacemaker applies pacing pulses to the patient's heart preferably varies linearly in the region between the base pacing rate and the maximum pacing rate, and is therefore characterized by a slope. The slope of the transfer function allows the pacemaker to deliver pacing pulses at a variable rate in accordance with variations in the sensor level index signals. Preferably, the pacemaker stores a "family" of transfer function slopes in the memory, ranging from a relatively gradual slope to a relatively steep slope. If the pacemaker is operating in accordance with a transfer function that has a gradual slope, changes in the pacing rate will accordingly be more gradual than if the slope were steeper.

Although the physician can telemetrically define the slope of the transfer function (preferably by selecting one of the slopes in the family of transfer function slopes stored in the memory) along with the base pacing rate, the maximum pacing rate, and other known pacing parameters, the physician's slope selection is not necessarily fixed. Rather, in the preferred embodiment of the invention, the pacemaker is capable of self-adjusting the slope based on certain information provided by the physician (i.e., the base pacing rate and the maximum pacing rate), and information reflecting the patient's activity profile over a predetermined period of time. After the rate-responsive pacemaker updates the slope, it can apply pacing pulses to the patient's heart using the new transfer function. By automatically adjusting the slope of the transfer function, the pacemaker advantageously minimizes the number of labor-intensive programming steps that may otherwise be necessary.

In order to obtain the slope, measurements of the patient's level of activity, preferably taken at regular intervals over a period of about one week, are stored in the memory in the form of an activity level histogram. The activity level histogram develops a peak count at an activity level that is roughly equal to the patient's average activity level. The average activity level is also preferably maintained in the memory as a running average, independently of the information stored in the activity level histogram. Since the typical patient is relatively inactive most of the time, the maintained average activity level approximately corresponds to the patient's resting activity level. For the typical patient, the programmed base pacing rate is appropriate when the patient is engaged in the average level of activity (i.e., it should not be necessary to increase the pacing rate from the base pacing rate when the patient is relatively inactive). Therefore, for the purpose of calculating the appropriate slope of the transfer function, it may be assumed that at average activity levels, pacing is performed at the base pacing rate. Preferably, this relationship is used to define a first point that is then used by the processing circuitry to derive the new slope.

However, before the processing circuitry can derive the new slope, another point of the transfer function needs to be defined. To that end, it has been experimentally found that for healthy subjects, the activity level that is exceeded one percent of the time correlates to the heart rate that is exceeded one percent of the time. It has further been found that a typical sedentary subject experiences heart rates above the upper twenty-fifth percentile of the subject's heart rate reserve only one percent of the time (heart rate reserve is defined as the range of heart rates available between the subject's average heart rate and the subject's maximum heart rate). For pacemaker patients, the base pacing rate may be substituted for the average heart rate (as described above), and the maximum pacing rate may be used as the maximum heart rate. Thus, the second point used by the processor circuitry may be defined by the level of activity that the patient exceeds one percent of the time, and the heart rate corresponding to the upper twenty-fifth percentile of the range between the base pacing rate and the maximum pacing rate. With two points of the new transfer function defined, the processing circuitry can derive the new slope.

In addition to storing the activity level measurements in the activity level histogram, activity deviation measurements are stored in the memory, preferably in the form of an activity deviation histogram. The activity deviation histogram is generated by calculating the difference between a current activity level measurement and a previous activity level measurement, with the difference value being stored in an appropriate bin of the activity deviation histogram. Preferably, like the activity level histogram, the activity deviation histogram is recycled weekly.

The activity deviation histogram is normally characterized by a bimodal distribution. The higher of the two modes reflects activity deviations corresponding to normal patient activity during the day. The lower mode, which is typically the dominant mode, reflects activity deviations that occur during sleep and rest. It has been determined that if a patient has been unusually inactive (i.e., bedridden) the weekly activity deviation histogram is characterized by a single mode that is similar to the dominant mode of the normal patient's activity deviation histogram. Thus, for the bedridden patient, there is a convergence of the peak activity deviation level and the median of the activity deviation measurements, as compared to similar values extracted from an activity deviation histogram for a normal patient. A similar effect also occurs with the activity level histogram, such that the activity level that is exceeded one percent of the time drops relative to the average activity level. If the slope of the transfer function were updated under these conditions, an undesirably steep slope might result if the base pacing rate and the maximum pacing rate were held constant. However, the pacemaker of the present invention can advantageously avoid this situation by blocking an update of the slope whenever the median of the activity deviation histogram is unusually close to the position of the dominant mode.

Another feature of the present invention allows pacemaker patients that participate in a regular exercise routine to reach their optimum target heart rate each time they exercise. Typically, a patient encounters the highest levels of activity for the week during periods of exercise. If a patient is known to exercise for a particular fraction of each week, then a corresponding fraction of the patient's measured activity levels can be assumed to correspond to the periods of exercise. For example, if the patient exercises 1.2 per cent of each week, then the highest 1.2 per cent of the measured activity levels collected in the activity level histogram during the week can be assumed to correspond to exercise. The physician can supply the pacemaker with the patient's target exercise heart rate. When the patient exercises, the measured activity levels fall into the upper 1.2 per cent of the activity level histogram. By adjusting the slope to account for the patient's target rate and the percentage of the week dedicated to exercise, the pacemaker can apply pacing pulses at the target heart rate during exercise.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which:

FIG. 1 is a schematic block diagram of a rate-responsive pacemaker which can automatically adjust a slope of a transfer function in accordance with the principles of the present invention;

FIG. 9 depicts an illustrative activity deviation histogram for a patient that has been engaged in relatively normal levels of activity;

FIG. 10 depicts an illustrative activity deviation histogram for a patient that has been unusually inactive;

FIG. 11 depicts an illustrative reaction time table used by the processor shown in FIG. 1 to limit the rate at which the pacing rate increases in response to an increase in physical activity;

FIG. 12 depicts an illustrative recovery time table used by the processor shown in FIG. 1 to limit the rate at which the pacing rate decreases in response to a decrease in physical activity.

DETAILED DESCRIPTION OF THE PREFERRED EMBODIMENTS

Figure 3:
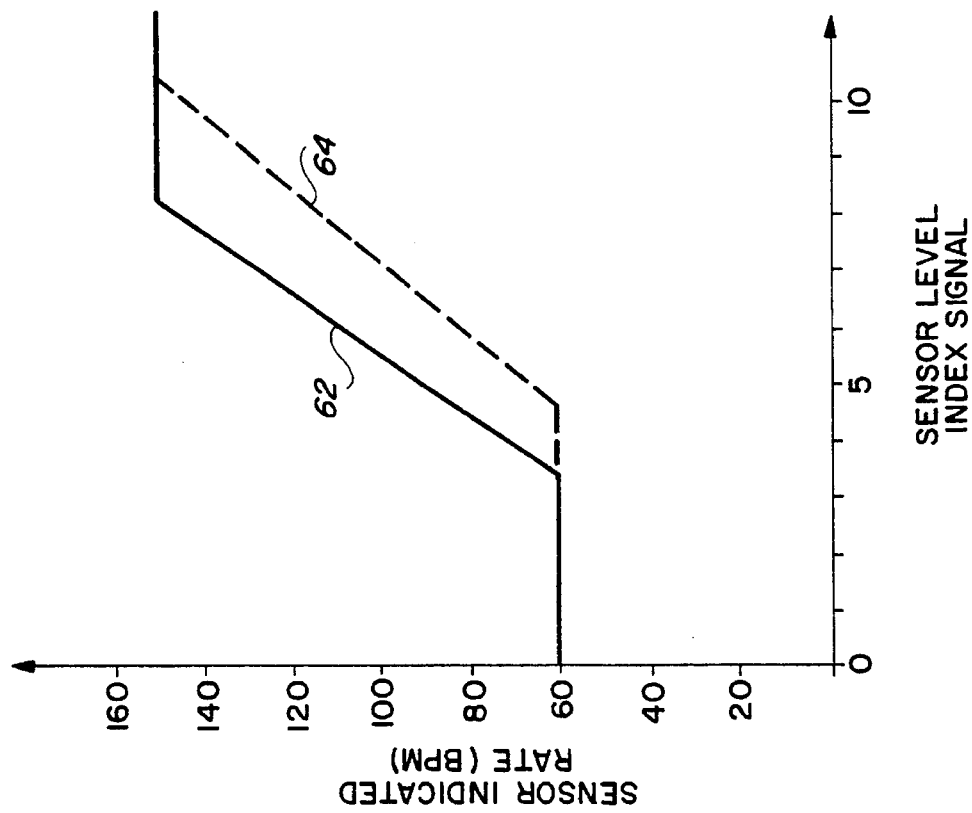
FIG. 3 illustrates the manner by which the rate-responsive pacemaker of FIG. 1 can automatically adjust the slope of the transfer function in accordance with the principles of the present invention.

Referring first to FIG. 1, a block diagram representing a rate-responsive pacemaker 20 configured in accordance with the principles of the present invention is described. In many respects, the pacemaker 20 operates in a conventional manner to provide pacing pulses at a rate that comfortably meets the patient's metabolic demands. More precisely, the pacemaker 20 uses signals generated by a piezoelectric physical activity sensor 22 to determine the extent to which the patient is engaged in physical activity—the measured level of activity being indicative of metabolic need. Any sensor that provides a suitable response to physical activity may be used as the sensor 22, including the activity sensors described in the above-incorporated U.S. patent applications Ser. Nos. 08/059,698 and 08/091,850. The principles of the present invention may also be applied to pacemakers which use other physiologic sensors to measure metabolic demand, such as blood oxygen sensors, pH sensors, temperature sensors, etc.

The signals generated by the sensor 22 are initially received by a sensor circuit 24. The sensor circuit 24 initially processes the rectified raw signals generated by the sensor 22 to provide digital sensor signals to a processor 26, which preferably includes a microprocessor (not shown). In a preferred embodiment, the sensor circuit 24 repeatedly integrates the raw sensor signals from the sensor 22 until a predetermined threshold is reached. Each time the threshold is reached, a digital trigger pulse is generated that increments a counter (not shown) of the sensor circuit 24.

The processor 26 determines the patient's level of activity by periodically examining the contents of the counter of the sensor circuit 24. Preferably, the processor 26 examines the contents of the counter once each heartbeat interval. To conserve power, the sensor circuit 24 is preferably powered for only a small fraction of each heartbeat interval. For example, the sensor circuit 24 may be powered for approximately 100 ms during each heartbeat interval. At the end of the 100 ms period, the processor 26 reads the contents of the counter and then resets the counter for the next heartbeat interval. The processor 26 uses the values read from the counter to determine sensor level index signals, in a manner described in greater detail below.

In addition to the sensor 22, the sensor circuit 24, and the processor 26, the pacemaker 20 includes a pacemaker circuit 28 (which may be conventional), and a memory 30 coupled to the processor 26. The pacemaker circuit 28 includes a pulse generator circuit 32, a timing and control circuit 34 coupled to the pulse generator circuit 22 and to the processor 26, and a telemetry circuit 36. The telemetry circuit 36, which telemetrically communicates with an external programmer 38, is coupled within the pacemaker 20 to the memory 30 and the timing and control circuit 34.

Coupled to the pulse generator circuit 32 is at least one conventional pacing lead 40 (although more pacing leads can be used if needed, as would be the case for a patient receiving dual-chamber pacing therapy). The pacing lead 40 is used to deliver pacing pulses provided by the pulse generator circuit 32 to the patient's heart 42. In addition, the pacing lead 40 senses the natural rhythm of the heart 42 (e.g., the patient's IEGM), and presents a signal indicative thereof to the timing and control circuit 34. The ability to sense the natural rhythm of the heart 42 enables the pacemaker 20 to operate in a demand mode, in which delivery of a pacing pulse is inhibited by the timing and control circuit 34 when a naturally occurring cardiac contraction is sensed during the escape interval following a preceding contraction.

Although the following description assumes that the pacemaker 20 operates in a demand mode, it should be understood that a simpler implementation is possible, in which the pacemaker 20 does not inhibit delivery of pacing pulses when naturally occurring contractions are sensed. Also, demand mode may be a telemetrically programmable feature, allowing the pacemaker 20 to be switched into and out of demand mode when desired by a physician.

In order to regulate the rate at which the pacemaker 20 delivers pacing pulses to the heart 42, the processor 26 provides a rate control signal to the timing and control circuit 34. The rate control signal provided by the processor 26 preferably adjusts the escape interval used by the timing and control circuit 34, which has the effect of changing the maintained heart rate. Increasing the escape interval decreases the maintained heart rate, because the pacemaker 20 gives the heart 42 more time to contract on its own before the next pacing pulse is delivered. Decreasing the escape interval has the opposite effect.

Figure 2:
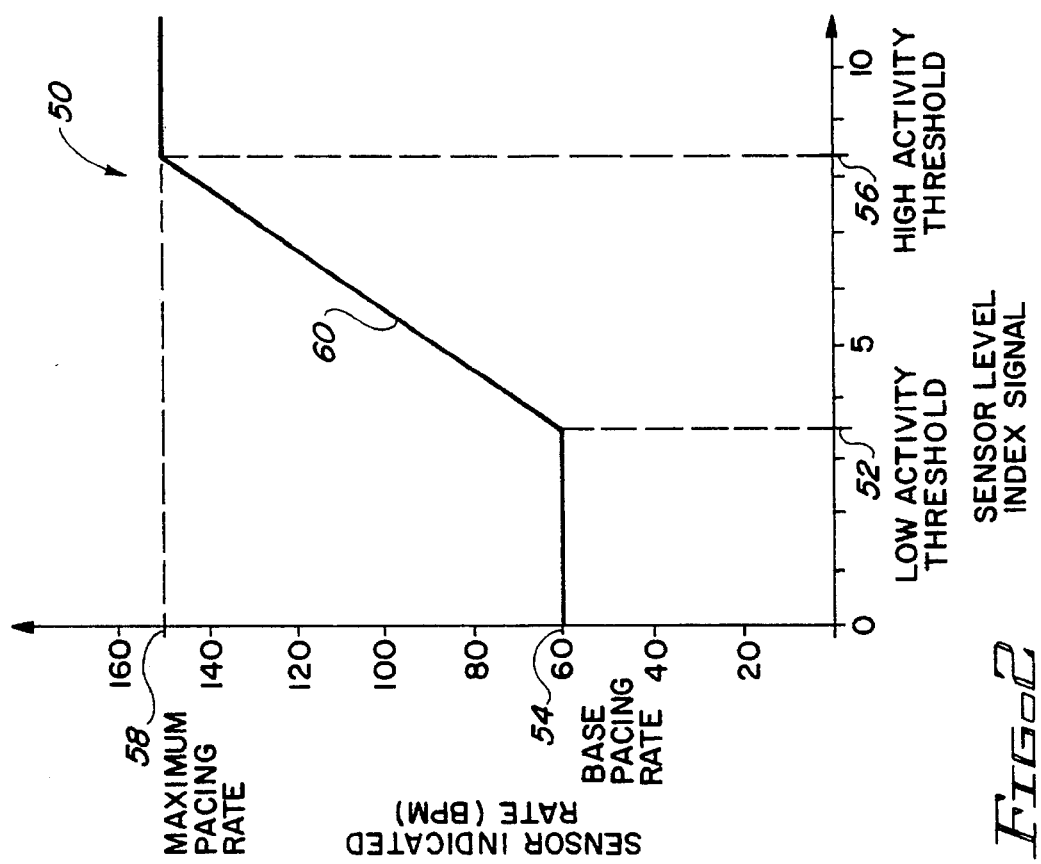
FIG. 2 is an illustrative transfer function for the rate-responsive pacemaker of FIG. 1, which correlates levels of physical activity to pacing rates.

Referring now to FIG. 2, an illustrative transfer function 50 for a rate-responsive pacemaker is described so that the principles of the present invention may be better understood. The transfer function 50 may be used by the processor 26 (FIG. 1) to correlate sensor level index signals (as derived by the processor 26 of FIG. 1) shown along the horizontal axis to sensor-indicated heart rates shown along the vertical axis.

For any sensor level index signal below a low activity threshold 52, the pacing rate is fixed at a base pacing rate 54, which is shown in the example of FIG. 2 to be about 60 bpm. For sensor level index signals above a high activity threshold 56, the pacing rate is maintained at a maximum pacing rate 58, shown in this case to be about 150 bpm. For sensor level index signals between the low activity threshold 52 and the high activity threshold 56, the pacing rate preferably varies linearly between the base pacing rate 54 and the maximum pacing rate 58 in accordance with a transition segment 60 of the transfer function 50. The slope of the transition segment 60 defines the extent to which the pacing rate changes as the sensor level index signal changes between the low activity threshold 52 and the high activity threshold 56.

Parameters which define the characteristics of the transfer function 50 may be telemetrically programmed by the physician through the use of the external programmer 38 (FIG. 1), the parameters then being stored in the memory 30 (FIG. 1) of the pacemaker 20 (FIG. 1). These parameters may include the low activity threshold 52, the base pacing rate 54, the high activity threshold 56, the maximum pacing rate, and the slope of the transition segment 60. However, in accordance with the principles of the present invention, the slope of the transition segment 60 is not necessarily fixed. Rather, if the physician so chooses, the slope may be automatically adjusted by the processor 26 (FIG. 1) on a periodic basis, to accommodate changes in the patient's activity profile.

In FIG. 3, an example is shown that generally depicts the manner by which the pacemaker 20 automatically adjusts the slope of a representative transfer function 62. The transfer function 62 may have been initially programmed by the physician (through the use of the above-described parameters), or may have been the result of a prior automatic adjustment.

While operating in accordance with the transfer function 62, the processor 26 (FIG. 1) acquires digital data representative of the patient's activity level from the sensor circuitry 24 (FIG. 1). As explained above, the processor 26 (FIG. 1) uses this information to derive sensor level index signals that it then uses to select an appropriate heart rate. In addition, certain digital activity measurements acquired by the processor 26 (FIG. 1) at predetermined intervals (preferably about every 26 seconds) over a predetermined period of time (preferably about a week) are stored in the memory 30 (FIG. 1), preferably in the form of a histogram.

Using the information stored in the memory 30 (FIG. 1), the processor 26 (FIG. 1) derives a new transfer function 64 that may better suit the patient's current activity profile. As compared to the transfer function 62, the new transfer function 64 is characterized by a smaller slope and larger low and high activity thresholds. However, the base pacing rate and the maximum pacing rate preferably do not change. Indeed, in a preferred embodiment of the invention, the base pacing rate and the maximum pacing rate, as programmed by the physician, are used by the processor 26 (FIG. 1) (along with the stored activity information) to derive the slope of the new transfer function 64.

Referring now to FIGS. 4–7, a series of logic flow diagrams are described which represent a control program executed by the processor 26 of FIG. 1. The control program enables the pacemaker 20 (FIG. 1) to provide rate-responsive pacing therapy, and it also advantageously allows the pacemaker 20 (FIG. 1) to adjust the slope of the transfer function in accordance with the patient's changing activity profile. In addition, the control program allows the pacemaker 20 (FIG. 1) to adjust the slope of the transfer function so that it accommodates the patient's regular exercise routine. Further, the control program inhibits the pacemaker 20 (FIG. 1) from automatically adjusting the slope of the transfer function when the patient has been unusually inactive (e.g., bedridden) for an extended period of time.

Figure 4:
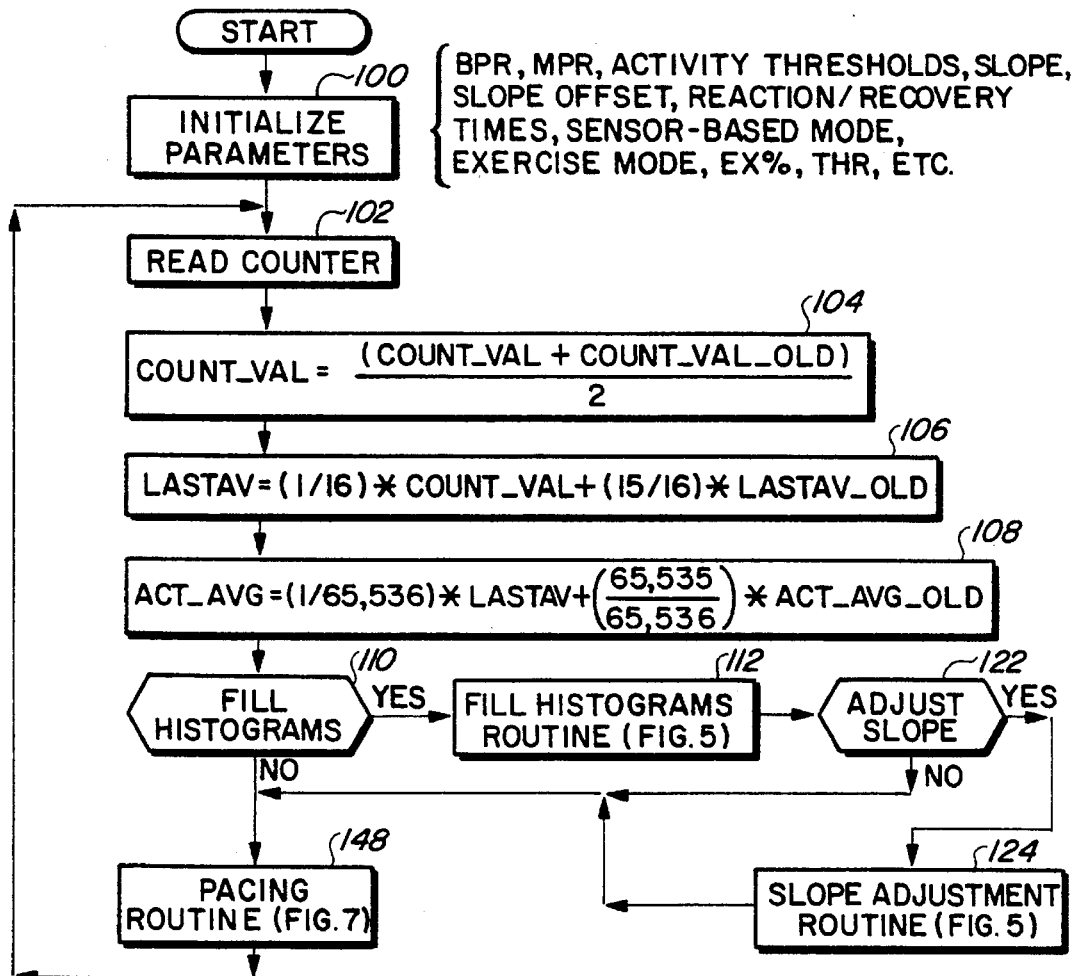
FIGS. 4–7 depict logic flow diagrams representing a control program used by the processor shown in FIG. 1 to automatically adjust the slope of the transfer function in accordance with the principles of the present invention.

Referring first to FIG. 4, the control program starts when a start-up command is received from the external programmer 38 (FIG. 1) through the telemetry circuit 36 (FIG. 1). This command may be sent in connection with the implantation procedure (before, during, or after), and during subsequent follow-up visits.

After start-up, the processor 26 (FIG. 1 performs an initialization step 100, at which the pacemaker 20 (FIG. 1) acquires operating parameters from the external programmer 38 (FIG. 1) through the telemetry circuit 36 (FIG. 1), the parameters then being stored in the memory 30 (FIG. 1). Many of the parameters received at the step 100 may be conventional (e.g., pulse width, pulse amplitude, etc.); however, several other parameters are used to implement the features of the present invention. For example, at the step 100, the physician can disable the automatic slope adjustment feature of the present invention, and can even disable rate-responsive pacing entirely. When a feature is disabled, the steps of the control program corresponding to those features are not performed by the processor 26 (FIG. 1).

The parameters that are used to implement the automatic slope adjustment feature of the present invention include base pacing rate (BPR), maximum pacing rate (MPR), slope, slope offset, and reaction and recovery times. The slope set at the step 100 may be used by the pacemaker 20 (FIG. 1) until a sufficient amount of activity data has been collected to set the slope in accordance with the patient's activity profile, or if the automatic slope adjustment feature has been disabled. As described below, the slope offset provides the physician with some control over the slope that is automatically determined by the processor 26 (FIG. 1). Also as explained below, the reaction and recovery times limit the rate at which the pacing rate may change in response to changes in the patient's measured level of activity.

In addition, the physician can set the pacemaker 20 (FIG. 1) to operate in an exercise mode, in which the processor 26 (FIG. 1) automatically sets the slope of the transfer function such that the patient's optimum heart rate for exercise is reached during periods of exercise. Additional parameters must be set for this feature at the step 100, including exercise percent (Ex%) and target heart rate (THR). The Ex% is set to the percentage of time that the patient spends exercising, preferably over a period of a week. The THR is set to the patient's optimal heart rate for exercise.

After the step 100, the processor 26 (FIG. 1) performs a sequence of steps 102–108 which are preferably re-executed during each heartbeat interval. At the step 102, the processor 26 (FIG. 1) reads the contents of the counter (not shown) of the sensor circuit 24 (FIG. 1), and stores the value in a variable designated as Count_Val. As explained above, the contents of the counter is a digital representation of the patient's activity level as measured during a predetermined period (preferably 100 ms) within the current heartbeat interval. At the step 102, the processor 26 (FIG. 1) also clears the counter in preparation for the next heartbeat interval.

In order avoid using a measurement that is uncharacteristically high or low, the processor 26 (FIG. 1) averages the current counter reading with the counter reading taken during the previous heartbeat interval, as shown in Equation 1.

$$\text{Count\_Val} = \frac{(\text{Count\_Val} + \text{Count\_Val\_Old})}{2} \quad (1)$$

The variable designated as Count_Val_Old is used to store the counter reading taken during the previous heartbeat cycle. However, during the first execution of the step 104 after start-up, Count_Val is effectively set equal to the current counter reading, since there no previous counter reading to average it with.

At the step 106, the value stored in Count_Val is digitally processed by the processor 26 (FIG. 1) using a recursive low-pass filter to derive a digitally smoothed representation of the patient's current activity level, as illustrated by Equation 2.

$$\text{LastAv} = (1/16) * \text{Count\_Val} + (15/16) * \text{LastAv\_Old} \quad (2)$$

The variable designated as LastAv contains the digitally smoothed representation of the patient's activity level. The variable designated as LastAv_Old represents the value of LastAv derived using Equation 2 during the previous cardiac cycle. At a heart rate of 72 bpm, the digital filter defined by Equation 2 has a time constant of approximately 13 seconds. During the first execution of the step 106, the variable LastAv is effectively set equal to the value of Count_Val.

At the step 108, the processor 26 (FIG. 1) uses the derived value of LastAv to derive a value, designed by the variable Act_Avg, representing the patient's average activity level. This is accomplished by applying a first order low-pass digital filter to the value of LastAv, as illustrated by Equation 3.

$$\text{Act\_Avg} = (1/65536) * \text{LastAv} + (65535/65536) * \text{Act\_Avg\_Old} \quad (3)$$

The variable designated as Act_Avg_Old represents the value of Act_Avg derived during the previous heartbeat cycle. At a pacing rate of 60 bpm, the time constant of this digital filter is approximately 18 hours. Thus, the variable Act_Avg represents a running average of the patient's activity level, which in turn closely approximates the patient's activity level at rest. During the first execution of the step 108 after start-up, the value of Act_Avg is effectively set equal to the value of LastAv computed at the step 106.

After the values have been computed for Count_Val, LastAv, and Act_Avg, the processor performs a test 110 to determine if it is time to store values in the memory 30 (FIG. 1) in the form of an activity level histogram and an activity deviation histogram. Preferably, the physician can select how frequently values are added to the histograms. However, to conserve memory, only a fraction of the computed values are stored. In a preferred embodiment, values are added to the histograms once every 26 seconds, rather than every heartbeat cycle. As explained below, the activity histograms are used to develop an activity profile for the patient, which in turn is used to automatically adjust the slope of the transfer function.

Figure 5:
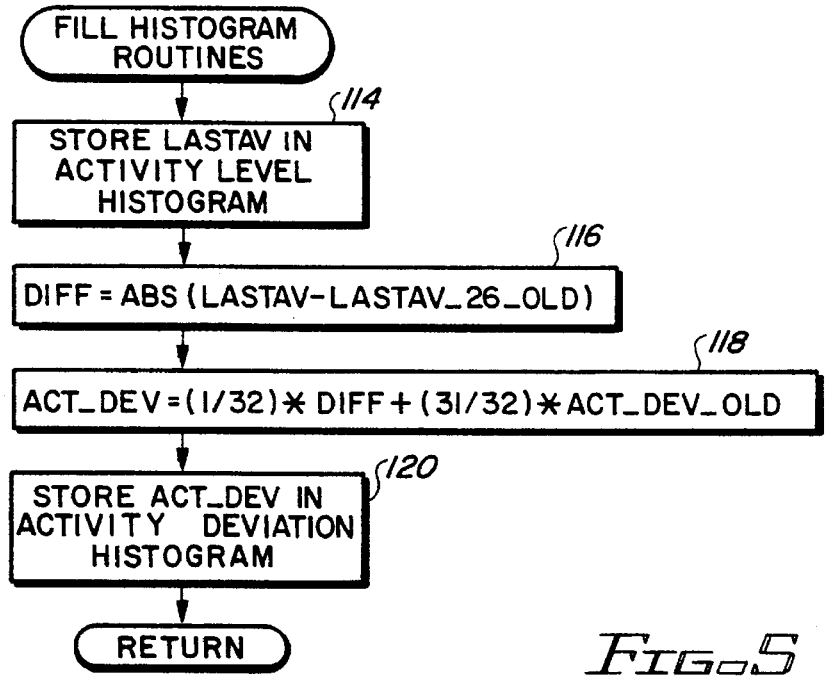

If the processor 26 (FIG. 1) determines at the test 110 that it is time to store values in the histograms, a step 112 is performed, at which a Fill Histograms routine is called. The Fill Histograms routine is shown in FIG. 5.

At a step 114 of the Fill Histograms routine, the value of LastAv computed at the step 106 (FIG. 4) is added to an appropriate bin of an activity level histogram. An activity level histogram 200 containing data collected over a period of about one week for a typical patient is shown in FIG. 8.

Figure 8:
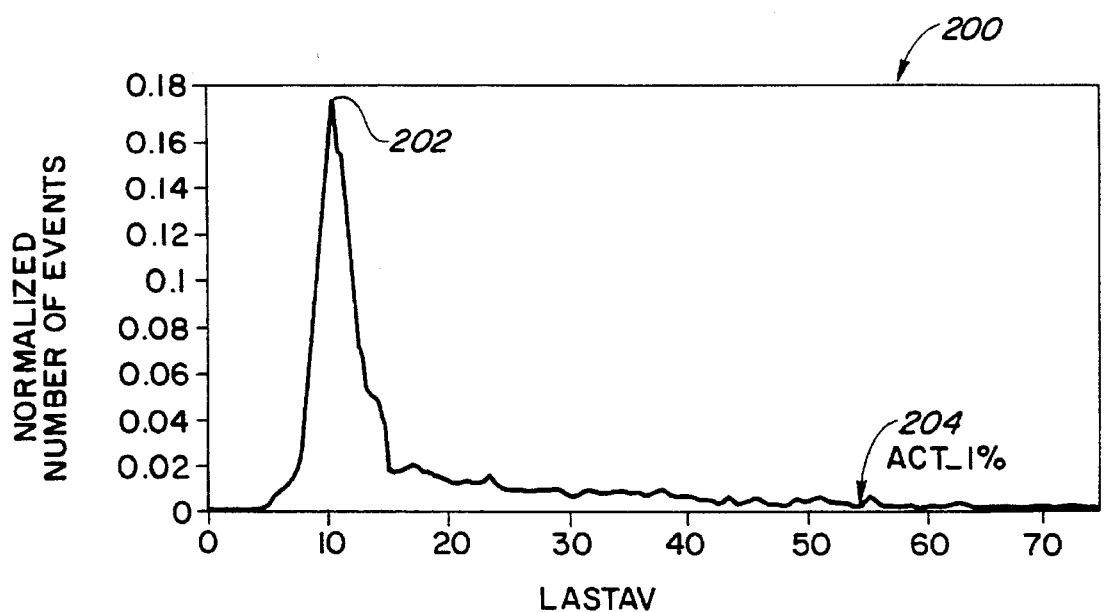
FIG. 8 depicts an illustrative activity level histogram used by the processor shown in FIG. 1 to automatically adjust the slope of the transfer function in accordance with the principles of the present invention.

Referring now to FIG. 8, the activity level histogram 200 is preferably divided into 256 two-byte bins, each of which is assigned a corresponding LastAv value. The activity level histogram 200 therefore occupies 512 bytes of the memory 30 (FIG. 1).

The first bin of the activity level histogram 200 is incremented when no activity is detected (i.e., LastAv is approximately equal to zero). Each successive bin corresponds to a slightly higher activity level (i.e., a slightly higher value for LastAv). If one bin in the histogram is incremented every 26 seconds, the histogram is sufficiently filled in about one week, at which point the slope of the transfer function can be updated, if desired, in a manner described below. One advantage of this approach is that slope adjustments are made based on an activity level histogram that accurately depicts the patient's activity profile over the course of a week.

Two features of the activity level histogram 200 are briefly noted at this point. First, the activity level histogram 200 exhibits a mode 202 in a bin corresponding to a relatively low value of LastAv. It has been found that the mode 202 approximately corresponds to the patient's average activity level, Act_Avg, as computed at the step 108 (FIG. 4). Second, a bin 204 is designated Act 1%. This bin corresponds to the upper first percentile of the patient's activity measurements (i.e., the highest 1% of LastAv values) computed over the course of the week. As explained below, these two values may be used by the processor 26 (FIG. 1), in connection with the preprogrammed BPR and MPR, to adjust the slope of the transfer function.

Preferably, in addition to storing the LastAv values as an activity level histogram, activity deviation values are stored in the memory 30 (FIG. 1) in the form of an activity deviation histogram. Referring again to FIG. 5, the activity deviation values are computed by the processor 26 (FIG. 1) in accordance with steps 116 and 118. At the step 116, the processor 26 (FIG. 1) computes a value, designated by the variable Diff, representing the absolute value of the difference between the current value of LastAv and the value of LastAv that was computed about 26 seconds earlier, as illustrated in Equation 4.

$$\text{Diff} = \text{ABS}(\text{LastAv} - \text{LastAv\_26\_Old}) \quad (4)$$

The variable designated as LastAv_26_Old contains the value of LastAv computed about 26 seconds earlier. During the first execution of the step 116 after start-up, the value of Diff is set equal to zero.

The difference computed at the step 116 is smoothed by the processor 26 (FIG. 1) at the step 118 using a first order recursive digital filter, as shown in Equation 5.

$$\text{Act\_Dev} = (1/32) * \text{Diff} + (31/32) * \text{Act\_Dev\_Old} \quad (5)$$

The variable designated as Act_Dev is used to store the current smoothed difference, and the variable designated as Act_Dev_Old is used to store the prior smoothed difference. During the first execution of the step 118 after start-up, the value of Act_Dev is effectively set equal to the value of Diff.

At a step 120, the value of Act_Dev computed at the step 118 is added to an appropriate bin of an activity deviation histogram. An activity deviation histogram 206 containing data collected over a period of about one week for a typical patient is shown in FIG. 9.

Referring now to FIG. 9, the activity deviation histogram 206 is preferably divided into 128 two-byte bins, each of which is assigned a corresponding Act_Dev value. The activity deviation histogram 206 therefore occupies 256 bytes of the memory 30 (FIG. 1).

The activity deviation histogram 206 is characterized by a bimodal distribution. A higher mode 208 of the two modes corresponds to activity deviations during the day. A lower mode 210, which is the dominant mode, corresponds to activity deviations measured during sleep. However, if the patient has been unusually inactive (e.g., bedridden) for a significant portion of the week, the two modes converge, and the activity deviation histogram becomes nearly unimodal. As explained below, this phenomenon may be used by the processor 26 (FIG. 1) to inhibit slope adjustments based on activity data collected while the patient was unusually inactive. Such an adjustment may result in undesirably steep slope which is likely to be inappropriate when the patient resumes normal activities.

After the processor 26 (FIG. 1) stores the most recent Act_Dev value in the activity deviation histogram at the step 120, control returns to the main program of FIG. 4. The processor 26 (FIG. 1) then performs a test 122 to determine if it is time to adjust the slope of the transfer function. Preferably, the processor 26 (FIG. 1) adjusts the slope on a weekly basis.

Figure 6:
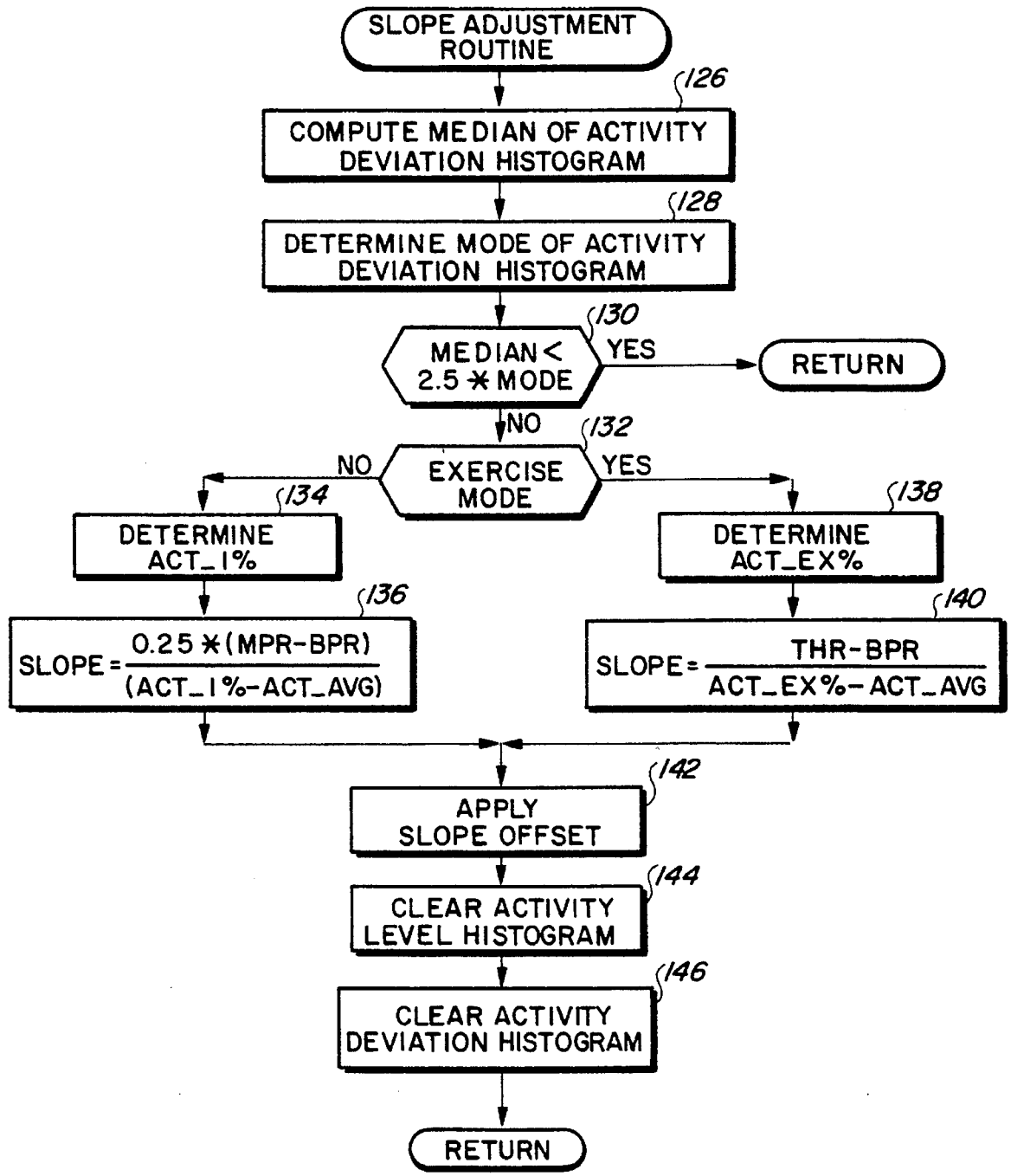

When it is time to adjust the slope, the processor 26 (FIG. 1) proceeds to a step 124 where it calls a Slope Adjustment routine, which is shown in FIG. 6. After calling the Slope Adjustment routine, the processor 26 (FIG. 1) performs steps 126 and 128, and a test 130 in order to determine if the patient has been unusually inactive during the past week. More precisely, at the step 126, the processor 26 (FIG. 1) determines the bin of the activity deviation histogram stored in the memory 30 (FIG. 1) that corresponds to the median of the activity deviation values stored during the past week. At the step 128, the processor 26 (FIG. 1) determines the bin of the activity deviation histogram corresponding to the dominant mode (i.e., the dominant mode 210 of FIG. 9).

As explained above in connection with FIG. 9, the activity deviation histogram 206 is representative of a normal patient, and is thus characterized by a bimodal distribution. However, if the patient was unusually inactive during the previous week (e.g., bedridden), the higher mode 208 converges on the dominant mode 210, leading to an almost unimodal distribution.

An activity deviation histogram 212 for an usually inactive patient is shown in FIG. 10. The activity deviation histogram 212 is characterized by a dominant mode 214, and there is little or no discernable higher mode. One result of this phenomenon is that the bin corresponding to the median of the activity deviation histogram 212 is much closer to the bin corresponding to the dominant mode 214 than is the case for an activity deviation histogram for a normal patient (i.e., the activity deviation histogram 206 of FIG. 9). More precisely, it has been found that if the bin corresponding to the median is less than about 2.5 times the bin corresponding to the dominant mode, the patient has likely been unusually inactive during the past week.

Referring again to FIG. 6, the processor 26 (FIG. 1) thus determines at the test 130 if the median of the activity deviation histogram is less than about 2.5 times the mode. If so, control is returned to the main program of FIG. 4, without an update of the slope of the transfer function. Thus, in accordance with the principles of the present invention, slope adjustments are advantageously inhibited when the patient has been unusually inactive. The pacemaker 20 (FIG. 1) may continue to use a slope that was set after a week of relatively normal activity, or one that was telemetrically set by the physician.

If the processor 26 (FIG. 1) determines at the test 130 that the patient has not been unusually inactive, a test 132 is performed to determine if the exercise mode was selected during the initialization step 100 (FIG. 4). If not, the processor 26 (FIG. 1) performs a step 134 where it determines the bin of the activity level histogram that corresponds, preferably, to the upper first percentile of the LastAv values stored during previous week.

Referring briefly again to the activity level histogram 200 of FIG. 8, the upper first percentile of LastAv values is shown as the bin 204, also designated by the variable Act_1%. In order to identify the bin that corresponds to the upper first percentile of LastAv values, the processor 26 (FIG. 1) adds the contents of each of the bins, starting with the highest bin and proceeding through successively lower bins until 233 events (approximately 1% of the total of 23296 events stored during the week) have been counted. The bin associated with the 233rd event corresponds to the upper first percentile of stored LastAv values. The LastAv value corresponding to the bin containing the 233rd event is thus designated Act_1%.

Referring again to FIG. 6, after determining the value of Act_1%, the processor 26 (FIG. 1) computes the new slope of the transfer function at a step 136 using Act_Avg (determined at the step 108 (FIG. 4)), Act_1% (determined at the step 134), and the preprogrammed values for BPR and MPR (initialized at the step 100 (FIG. 4)). So that the principles of the present invention may be better understood, a brief discussion of the theoretical basis supporting the relation shown in the step 136 is now provided.

As explained above, the variable Act_Avg is used to store a running average of the patient's activity level. The running average closely approximates the patient's resting level of activity. In a healthy individual, an average level of activity should correspond to an average heart rate, the average heart rate being appropriate for the individual at rest. For pacemaker patients, there should be no need to elevate the pacing rate from the BPR if the patient is at rest (i.e., if the current level of activity is about the same as Act_Avg). Therefore, for the purpose of calculating the slope of the transfer function, it is reasonable to assume that at an activity level of Act_Avg, the pacing rate should be set to the BPR.

It is also reasonable to assume that for a healthy individual, the highest heart rates are associated with the highest levels of activity, and more precisely, that the highest one percent of heart rates are associated with highest levels of activity attained by such individuals only one percent of the time. Thus, for a pacemaker patient, the highest pacing rates attained only one percent of the time (pacing rates that meet or exceed a rate designated as HR_1%) should be associated with levels of activity that meet or exceed Act_1%. Because an activity level of Act_Avg should result in pacing at the BPR, and because an activity level of Act_1% should result in a sensor-indicated rate of HR_1%, the slope of the transfer function can be calculated using Equation 6.

$$\text{Slope} = (\text{HR\_1\%} - \text{Base\_Rate}) / (\text{Act\_1\%} - \text{Act\_Avg}) \qquad (6)$$

The unknown in Equation 6—HR_1%—has been empirically determined by analyzing heart rate data from members of a training group of healthy individuals. The data revealed that a typical sedentary subject spends 99% of the time at heart rates that are below the upper twenty-fifth percentile of the subject's heart rate reserve (heart rate reserve being defined as the heart rates available between the subject's maximum heart rate and resting heart rate). Thus, HR_1% can be estimated to be 25 percent of the difference between the subject's maximum heart rate and the resting heart rate, added to the resting heart rate. In order to estimate an appropriate slope for a pacemaker patient, HR_1% was therefore taken to be the sum of the BPR and 25 percent of the difference between the MPR and the BPR. Substituting this relationship into Equation 6 yields Equation 7.

$$\text{Slope} = \frac{0.25 * (\text{MPR} - \text{BPR})}{(\text{Act\_1\%} - \text{Act\_Avg})} \quad (7)$$

Using Equation 7, the appropriate slope of the transfer function can be calculated by the processor 26 (FIG. 1) at the step 136. Equation 7 was tested with subjects who were not in the original training group, and it was found to yield satisfactory slopes for the transfer function.

The slope determined at the step 136 may be used directly by the processor 26 (FIG. 1) to determine appropriate heart rates in accordance with physical activity. However, in a preferred embodiment, the slope value obtained at the step 136 is applied to a look-up table (not shown) stored in the memory 30 (FIG. 1). The look-up table correlates the computed slope value to one of a family of available slopes stored in the memory 30 (FIG. 1). Preferably, a family of sixteen slopes are available for selection in the memory 30 (FIG. 1).

If, at the test 130, the processor 26 (FIG. 1) determines that exercise mode was selected, a step 138 is performed to determine the bin of the activity level histogram that corresponds to the exercise percentage (Ex%) entered at the initialization step 100 (FIG. 4). In many respects, the step 138 is similar to the step 134—the difference being that instead of counting the highest one percent of events in the activity level histogram, the number of events counted is determined by Ex%. For example, if a patient is known to exercise for two hours per week, the physician would enter 1.2% as the Ex% at the step 100 (FIG. 4), because two hours corresponds to about 1.2% of each week. Using this example, the processor 26 (FIG. 1) would count down from the highest bin until the highest 1.2% of the stored events have been counted. The bin corresponding to the highest Ex% of events is stored in a variable designated as Act_Ex%.

Since it is ordinarily desirable for the patient to reach the target heart rate (THR) during each exercise session, the combination of Act_Ex% and the THR (as entered at the initialization step 100 (FIG. 4)) defines one point for computing the slope of the transfer function. The other point is defined by the combination of the BPR and Act_Avg, as described for the step 136. Thus, a slope that advantageously accommodates the patient's exercise routine may be computed by the processor 26 (FIG. 1) at a step 140 in accordance with Equation 8.

$$\text{Slope} = \frac{(\text{THR} - \text{BPR})}{(\text{Act\_Ex\%} - \text{Act\_Avg})} \quad (8)$$

Of course, the values provided for the THR and Ex% can be modified at the initialization step 100 (FIG. 4) to suit the needs of a particular patient.

After the slope has been computed (either at the step 136 or the step 140), the processor 26 (FIG. 1) proceeds to a step 142, where it applies a slope offset to the computed slope, if a slope offset was provided at the initialization step 100 (FIG. 1). The slope offset provides the physician with even more control over the slope that is ultimately used to select pacing rates than that provided through the selection of the BPR and the MPR.

As explained above, in the preferred embodiment of the invention, the slope initially determined by the processor 26 (FIG. 1) (either at the step 136 or the step 140) is used to select a particular slope from a discrete family of slopes stored in the memory 30 (FIG. 1). The slope offset causes the processor 26 (FIG. 1) to select a slope that is somewhat different from the one that would otherwise be selected. For example, if the family of slopes included 16 different slopes numbered one through sixteen from the most gradual to the most steep, and the slope selected in accordance with the step 136 or the step 140 is slope #4, and the slope offset is set at +2, then the slope used in connection with rate-responsive pacing would be slope #6, not slope #4. For a variety of reasons, the physician may feel that a steeper slope is more appropriate. Of course, the slope offset may be set such that a slope is selected that is more gradual than the computed slope.

After the slope offset is applied, the processor 26 (FIG. 1) clears the activity level histogram at a step 144 and clears the activity deviation histogram at a step 146. The histograms are then ready to collect new data over the next week. Control then returns to the main program of FIG. 4.

Figure 7:
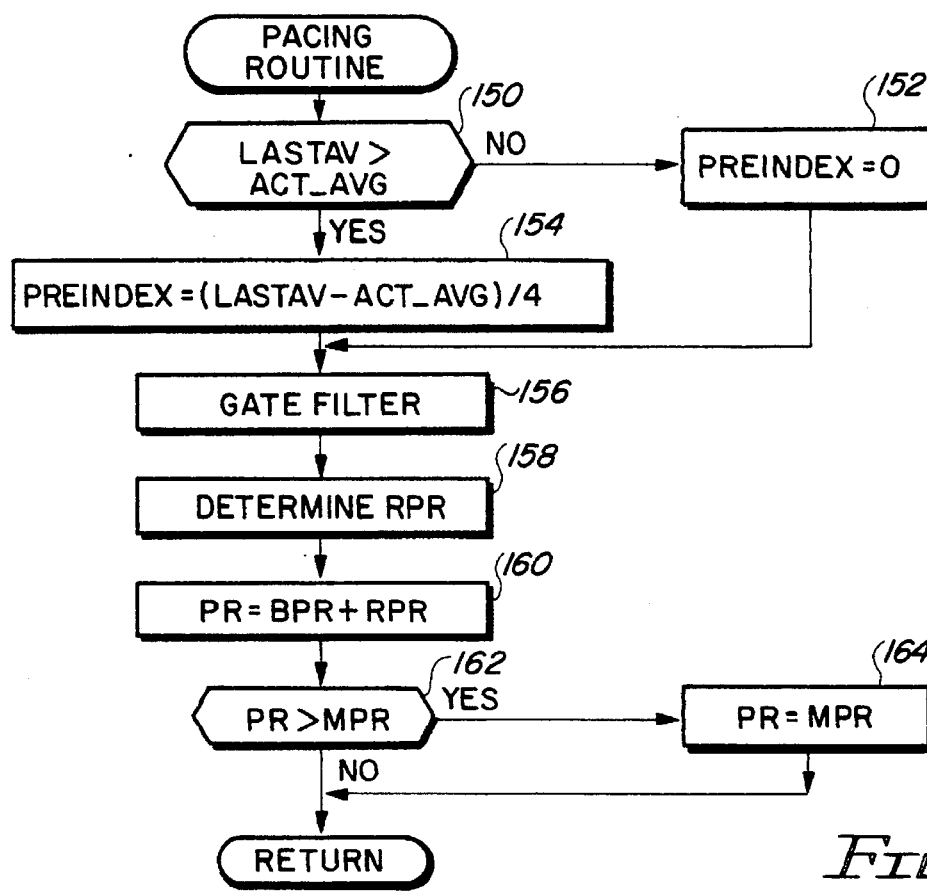

Referring again to FIG. 4, if it is determined at the test 110 that it is not time to fill the histograms, or it is determined at the test 122 that it is not time to adjust the slope, or after the step 124 is performed, the processor 26 (FIG. 1) proceeds to a step 148 where it calls a Pacing routine, which is shown in FIG. 7.

Referring now to FIG. 7, the Pacing routine starts with a test 150 where the processor 26 (FIG. 1) determines whether the value of LastAv computed at the step 106 (FIG. 4) exceeds the value of Act_Avg computed at the step 108 (FIG. 4). If not, the processor 26 (FIG. 1) proceeds to a step 152 where it sets a variable designated as PreIndex equal to zero. Otherwise, the processor 26 (FIG. 1) proceeds to a step 154 where it sets the value of PreIndex equal to the difference between the values of LastAv and Act_Avg, as illustrated by Equation 9.

$$\text{PreIndex} = (\text{LastAv} - \text{Act\_Avg})/4 \quad (9)$$

The variable PreIndex represents an instantaneous relative sensor level index signal, which may be used to define a pacing rate for the current cardiac cycle. More precisely, the value of PreIndex represents the amount by which the patient's current level of physical activity exceeds the average level of activity, as defined by Act_Avg. Since the pacing rate is increased from the base pacing rate only when the sensor level index value is greater than zero (as described below), the processor 26 (FIG. 1) advantageously uses the value of Act_Avg as the low activity threshold for the transfer function of the pacemaker 20 (FIG. 1). Like the slope of the transfer function, the low activity threshold is therefore not necessarily fixed. Rather, the low activity threshold changes in accordance with changes in the patient's activity profile.

Although the value of PreIndex may be used to define a pacing rate for the current heartbeat cycle, in a preferred embodiment, the value of PreIndex is passed through an asymmetric slew rate limiting filter (referred to as a gate filter) at a step 156 to derive a filtered relative sensor level index signal, designated by the variable INX. The purpose of the gate filter is to impose limits on the rate at which the processor 26 (FIG. 1) can alter the pacing rate from one heartbeat cycle to the next. Through the use of the gate filter, the pacemaker 20 (FIG. 1) is able to respond to short-term changes in the patient's activity level in a manner that more closely approximates the behavior of a properly functioning heart. For example, if the patient's activity level rapidly increases from a level corresponding to a heart rate of 60 bpm to a level that would ordinarily correspond to a heart rate of 150 bpm, it may be uncomfortable, and even dangerous, if the heart rate were to change as rapidly as the change in activity level.

The operation of the gate filter may be better understood by reference to the reaction time table shown in FIG. 11 and the recovery time table shown in FIG. 12. In FIG. 11, the left-most column shows that in this embodiment, there are sixteen possible slopes to choose from (either through automatic adjustment or manual selection). Each of the sixteen possible slopes may be associated with one of four possible reaction times—very fast, fast, medium, and slow. The reaction times need not be the same for different slopes (i.e., separate reaction times may be programmed for each slope). Each value in parentheses is the actual time (in seconds) required for the pacing rate to increase from 60 bpm to 150 bpm. For example, if the reaction time is programmed to "slow" for slope #9, it would take 39.4 seconds to increase the pacing rate from 60 bpm to 150 bpm.

The numerator of each fractional value in the reaction time table (preceding each parenthetical value) represents the number of heartbeat cycles during which the value of INX remains fixed following an increase in activity. The denominator represents the amount by which the value of INX is increased after the number of heartbeat cycles defined by the numerator has elapsed.

As an example, assume that the patient has been engaged in a constant level of activity for a long period of time corresponding to a PreIndex value of five. Also assume that the pacemaker 20 (FIG. 1) is operating in accordance with slope #9 with a reaction time of "slow." After a certain period of time (defined by the programmed reaction and recovery times) the value of INX reaches the value of PreIndex. If the patient suddenly engages in a much higher level of activity (for example, a level of activity corresponding to a PreIndex value of 15), the variable PreIndex responds very rapidly by virtue of the operation of Equation 9. However, it takes 25 heartbeat cycles for the value of INX to reach the new value of PreIndex (assuming the patient's activity level remains constant at the new higher level), because the processor 26 (FIG. 1) increments the value of INX by only units every five heartbeat cycles.

The concept of recovery time is similar to reaction time, with a few key exceptions. As shown in FIG. 12, there are preferably only three possible recovery times (fast, medium, and slow) for each possible slope, not four. Each number in parentheses represents the time required for the heart rate to change from 150 bpm to 60 bpm in response to a decrease in activity level. The number preceding each parenthetical value represents the number of heartbeat cycles required before the processor 26 (FIG. 1) decrements the value of INX by one unit.

Referring again to FIG. 7, the processor 26 (FIG. 1) proceeds to a step 158 where it uses the value of INX derived at the step 156 to determine a relative pacing rate (RPR) in accordance with the currently active slope of the transfer function. The relative pacing rate is the amount by which the BPR must be increased to accommodate a level of physical activity above Act_Avg.

Figure 13:
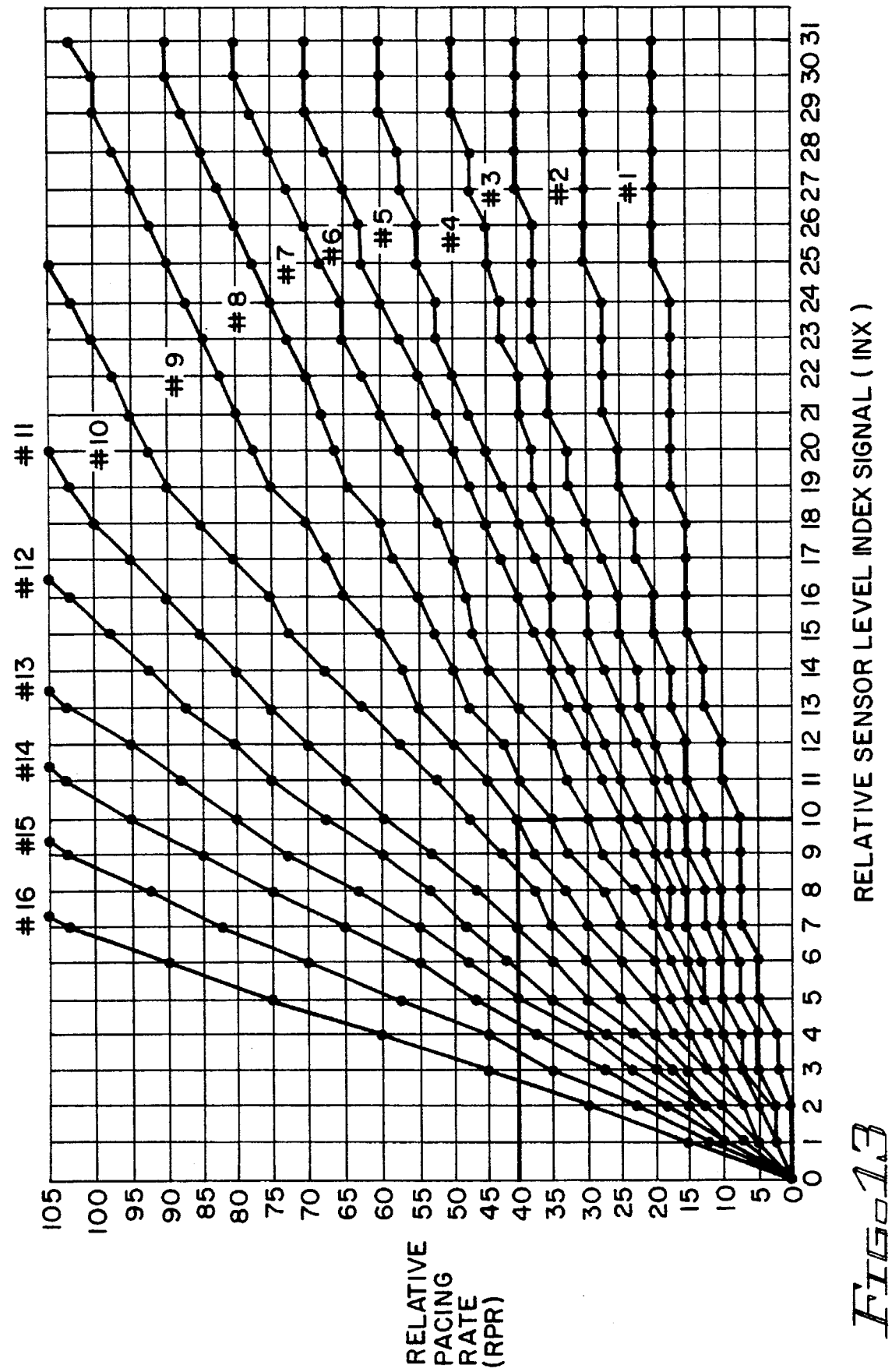
FIG. 13 depicts an illustrative family of transfer function slopes from which a slope may be automatically selected in accordance with the principles of the present invention.

The manner by which processor determines an appropriate RPR may be better understood by reference to the graph shown in FIG. 13. The graph depicts a family of sixteen discrete slopes which correlate sensor level index (INX) values (shown on the horizontal axis) with relative pacing rate (RPR) values (shown on the vertical axis). If the currently active slope is slope #9 (as determined at the step 142 (FIG. 6)) and the current value of INX is 10, the RPR is set to 40 bpm. If the current value of INX is zero, the RPR is set to zero, regardless of which slope is currently active.

Referring again to FIG. 7, the processor 26 (FIG. 1) proceeds to a step 160 where it computes an appropriate pacing rate, designated by the variable PR, using the preprogrammed BPR and the RPR determined at the step 158, as illustrated by Equation 10.

$$PR=BPR+RPR \qquad (10)$$

Through the operation of Equation 10, the PR is increased from the BPR by an amount defined by the RPR. Thus, if the patient is engaged in an average level of activity, the PR is set to the BPR, because the RPR is set equal to zero. (Of course, there may be a delay before the PR falls to the BPR after the patient's level of activity falls to the average level from a higher level, as described in connection with the recovery time table of FIG. 12.) Then, at a test 162, the processor 26 (FIG. 1) determines whether the PR determined at the step 160 exceeds the preprogrammed MPR. If not, control returns to the main program of FIG. 4. Otherwise, at a step 164, the PR is set to the MPR, and then control returns to the main program of FIG. 4.

After a pacing pulse is delivered (if required) in accordance with the newly determined PR (preferably by adjusting the escape interval), the program loops back to the step 104 to begin the next heartbeat cycle.

Thus, a rate-responsive pacemaker is provided that allows the slope of the transfer function to be automatically selected. The rate-responsive pacemaker measures a patient's level of activity and stores the results in an activity level histogram. The patient's average level of activity is maintained as a running average. Based on the physician-selected base and maximum pacing rates, the average level of activity, and the patient's activity profile stored in the activity level histogram, the rate-responsive pacemaker automatically calculates the slope of the pacemaker transfer function. An activity deviation histogram is also maintained. Analysis of this histogram allows the pacemaker to determine if the patient has been unusually inactive (e.g., bedridden) and should therefore not be provided with an automatically updated transfer function slope. If a patient desires to reach a target heart rate during exercise, the target heart rate and the fraction of time each week that the patient devotes to exercise can be programmed into the pacemaker to provide this feature.

One skilled in the art will appreciate that the present invention can be practiced by other than the described embodiments, which are presented for the purposes of illustration and not of limitation, and the present invention is limited only by the claims that follow.

What is claimed is:

1. A rate-responsive pacemaker for administering pacing pulses to a patient's heart in accordance with a predetermined transfer function that correlates sensor measurements representative of the patient's level of metabolic need to heart rate, the transfer function being having a base pacing rate, a maximum pacing rate, and a slope defining pacing rates between the base pacing rate and the maximum pacing rate, the rate-responsive pacemaker comprising:

a pulse generator for generating pacing pulses at a selectable rate between the base pacing rate and the maximum pacing rate in accordance with the predetermined transfer function;

a physiological sensor for generating raw sensor signals indicative of a patient's level of metabolic need;

a memory for storing the predetermined transfer function, and for storing selected sensor measurements as a first histogram, the first histogram representing a profile of the patient's level of metabolic need over a predetermined period of time, the first histogram defining a frequency distribution of sensor measurements for a plurality of amplitudes; and a processor, coupled to the pulse generator, the physiological, and the memory, for controlling the rate of pacing pulses, the processor including:
 (a) means for processing the raw sensor signals to derive the sensor measurements;
 (b) means for determining an appropriate heart rate for the patient's level of metabolic need based on the sensor measurements and the corresponding heart rate defined by the transfer function;
 (c) means for causing the pulse generator to generate pacing pulses at the appropriate heart rate;
 (d) means for selecting sensor measurements for storage in the first histogram; and
 (e) means for deriving the slope of the transfer function as a function of the patient's profile of metabolic need as represented by the first histogram containing the selected sensor measurements stored over the predetermined period of time.

2. The pacemaker of claim 1, wherein:

the memory further includes means for storing the base pacing rate and the maximum pacing rate;

the processor includes means for maintaining a running average of the sensor measurements in the memory; and the processor includes means for determining the slope of the transfer function in accordance with the base pacing rate, the maximum pacing rate, the running average, and the patient's profile of metabolic need as represented by the first histogram containing the selected sensor measurements stored over the predetermined period of time.

3. The pacemaker of claim 2, wherein the means for maintaining the running average includes means for digitally filtering the sensor measurements using a time constant of about 18 hours.

4. The pacemaker of claim 2, wherein:

the memory includes means for storing the first histogram using a plurality of storage locations corresponding to a plurality of bins, each bin associated with a different sensor measurement; and the processor includes means for incrementing a count associated with a particular bin when the sensor measurement to be stored in the first histogram corresponds to the particular bin.

5. The pacemaker of claim 4, wherein the processor includes means for deriving the slope of the transfer function in accordance with the relationship:

$$Slope = \frac{c * (MPR - BPR)}{(Act\_x\% - Act\_Avg)},$$

wherein:

MPR represents the maximum pacing rate;

BPR represents the base pacing rate;

Act_Avg represents the running average of the sensor measurements;

x% represents a percentage of total counts stored in the first histogram, which is preprogrammed into the memory;

Act_x% represents a bin of the first histogram corresponding to a sensor measurement that is exceeded by no more than a percentage designated by x% of the sensor measurements stored as counts in the first histogram over the predetermined period of time; and c is an empirically derived constant, preprogrammed into the memory, that defines a heart rate as a percentage of the difference between the maximum pacing rate and the base pacing rate, added to the base pacing rate, that should be achieved when the patient is experiencing a level of metabolic need defined by a sensor measurement designated by Act_x%.

6. The pacemaker of claim 5, wherein the processing means further includes means for deriving the slope using:

x% equal to about one percent; and c equal to about 0.25.

7. The pacemaker of claim 1, wherein the processor includes means for deriving the slope of the transfer function in accordance with the patient's regular exercise routine.

8. The pacemaker of claim 7, wherein:

the memory further includes means for storing the base pacing rate, and a target heart rate that is appropriate when the patient is engaged in exercise;

the processor includes means for maintaining a running average of the sensor measurements in the memory; and the processor includes means for deriving the slope of the transfer function in accordance with the base pacing rate, the target heart rate, the running average, and the patient's profile of metabolic need as represented by the first histogram containing the selected sensor measurements stored over the predetermined period of time.

9. The pacemaker of claim 8, wherein the means for maintaining the running average includes means for digitally filtering the sensor measurements using a time constant of about 18 hours.

10. The pacemaker of claim 8, wherein:

the first histogram comprises a plurality of bins, each bin associated with a different sensor measurement; and the processor includes means for incrementing a count associated with a particular bin when the sensor measurement to be stored in the first histogram corresponds to the particular bin.

11. The pacemaker of claim 10, wherein the processor includes means for deriving the slope of the transfer function in accordance with the relationship:

$$Slope = \frac{(THR - BPR)}{(Act\_Ex\% - Act\_Avg)},$$

wherein:

THR represents the target heart rate;

BPR represents the base pacing rate;

Act_Avg represents the running average of the sensor measurements;

Ex% represents a percentage of the predetermined period of time that the patient engages in exercise, which is preprogrammed into the memory; and Act_Ex% represents a bin of the first histogram corresponding to a sensor measurement that is exceeded by no more than a percentage designated by Ex% of the sensor measurements stored as counts in the first histogram over the predetermined period of time.

12. The pacemaker of claim 1, wherein the processor includes means for inhibiting the derivation of the slope of the transfer function when the patient's level of metabolic need is below a threshold level over the predetermined period of time.

13. The pacemaker of claim 12, wherein:

the memory further includes means for storing sensor measurement deviation values as a second histogram over the predetermined period of time, the second histogram having a dominant mode and a median; and the processor includes means for inhibiting the derivation of the slope of the transfer function when the median is less than about 2.5 times the mode after the predetermined period of time has elapsed.

14. The pacemaker of claim 13, wherein the processor includes means for deriving each sensor measurement deviation value by taking an absolute value of a difference between a current sensor measurement and an earlier sensor measurement.

15. The pacemaker of claim 14, wherein the processor includes means for deriving the current sensor measurement about 26 seconds after the the earlier sensor measurement.

16. The pacemaker of claim 1, wherein the processor includes means for periodically deriving the slope of the transfer function.

17. The pacemaker of claim 1, wherein the memory for storing the selected sensor measurements over a predetermined period of time includes means for storing the selected sensor measurements over about one week.

18. The pacemaker of claim 1, wherein:

the physiological sensor comprises an activity sensor; and the sensor measurements derived by the processor represent levels of physical activity, the levels of physical activity being indicative of the levels of metabolic need.

19. The pacemaker of claim 1, wherein:

the memory further includes means for storing a slope offset value; and the processor includes means for adding the slope offset value to the derived slope.

20. The pacemaker of claim 1, wherein the base pacing rate and the maximum pacing rate have a minimum and a maximum sensor threshold associated therewith, respectively, the first histogram further being characterized as having a mode with a first amplitude value associated therewith corresponding to the patient's average metabolic need, and a second amplitude value at the upper end of the first histogram corresponding to an upper value for the patient's metabolic need, further comprising:

means for adjusting the minimum sensor threshold to the first amplitude value; and means for adjusting the maximum sensor threshold to the second amplitude value.

21. A rate-responsive pacemaker comprising:

pulse generating means for generating pacing pulses at a selectable rate;

physiological sensing means for sensing a patient's level of metabolic need;

rate selecting means for selecting the rate at which the pulse generating means generates pacing pulses based on the sensed level of metabolic need and the corresponding heart rate defined by a transfer function that correlates metabolic need to heart rate, the transfer function comprising a slope that defines pacing rates between a minimum pacing rate and a maximum pacing rate;

slope adjusting means for automatically adjusting the slope of the transfer function in accordance with the level of metabolic need sensed over a predetermined period of time; and inhibiting means for inhibiting the slope adjusting means from automatically adjusting the slope of the transfer function when the patient's level of metabolic need over the predetermined period of time is below a threshold level.

22. The pacemaker of claim 21 further comprising:

memory means for storing sensor deviation values as a histogram over the predetermined period of time, the histogram having a dominant mode and a mean; and sensor deviation deriving means for deriving the sensor deviation values at predetermined intervals;

wherein the inhibiting means inhibits the slope adjusting means from adjusting the slope of the transfer function when the median is less than about 2.5 times the mode after the predetermined period of time has elapsed.

23. The pacemaker of claim 22, wherein the sensor deviation deriving means includes:

means for deriving each sensor deviation value by taking an absolute value of a difference between a current level of metabolic need sensed by the physiological sensing means and an earlier level of metabolic need sensed by the physiological sensing means.

24. The pacemaker of claim 23, wherein the processor includes means for deriving the current level of metabolic need about 26 seconds after the earlier level of metabolic need.

25. The pacemaker of claim 21, wherein the slope adjusting means includes means for periodically adjusting the slope of the transfer function.

26. The pacemaker of claim 21, wherein the memory for storing the selected sensor measurements over a predetermined period of time includes means for storing the selected sensor measurements over about one week.

27. The pacemaker of claim 21, wherein the physiological sensing means comprises activity sensing means for generating signals representative of levels of physical activity, the levels of physical activity being indicative of the levels of metabolic need.

28. A method of providing rate-responsive pacing therapy to a patient's heart in accordance with a transfer function that correlates sensor measurements representative of the patient's metabolic need to heart rate, the transfer function being having a base pacing rate, a maximum pacing rate, and a slope defining pacing rates between the base pacing rate and the maximum pacing rate, the method comprising the steps of:

generating pacing pulses at a selectable rate;

sensing a patient's level of metabolic need and generating raw sensor signals representative thereof;

processing the raw sensor signals to derive sensor measurements;

determining an appropriate heart rate for the patient's level of metabolic need based on the sensor measurements and the corresponding heart rate defined by the transfer function;

selecting sensor measurements for storage in the first histogram;

storing the selected sensor measurements as a first histogram, the first histogram representing a profile of the patient's metabolic need over a predetermined period of time, the first histogram defining a frequency distribution of sensor measurements for a plurality of amplitudes; and deriving the slope of the transfer function as a function of the patient's profile of metabolic need as represented by the first histogram containing the selected sensor measurements stored over the predetermined period of time.

29. The method of claim 28, wherein:

the method further comprises the step of maintaining a running average of the sensor measurements; and the deriving step comprises the step of deriving the slope of the transfer function in accordance with the base pacing rate, the maximum pacing rate, the running average, and the patient's profile of metabolic need as represented by the first histogram containing the selected sensor measurements stored over the predetermined period of time.

30. The method of claim 29, wherein maintaining step comprises the step of digitally filtering the sensor measurements using a time constant of about 18 hours.

31. The method of claim 29, wherein:

the memory includes means for storing the first histogram using a plurality of storage locations corresponding to a plurality of bins, each bin associated with a different sensor measurement; and the storing step comprises the step of incrementing a count associated with a particular bin when the sensor measurement to be stored in the first histogram corresponds to the particular bin.

32. The method of claim 31, wherein the deriving step comprises the step of deriving the slope of the transfer function in accordance with the relationship:

$$\text{Slope} = \frac{c * (\text{MPR} - \text{BPR})}{(\text{Act\_x\%} - \text{Act\_Avg})},$$

wherein:

MPR represents the maximum pacing rate;

BPR represents the base pacing rate;

Act_Avg represents the running average of the sensor measurements;

x% represents a predetermined percentage of total counts stored in the first histogram;

Act_x% represents a bin of the first histogram corresponding to a sensor measurement that is exceeded by no more than a percentage designated by x% of the sensor measurements stored as counts in the first histogram over the predetermined period of time; and c is a predetermined, empirically derived constant that defines a heart rate as a percentage of the difference between the maximum pacing rate and the base pacing rate, added to the base pacing rate, that should be achieved when the patient is experiencing a level of metabolic need defined by a sensor measurement designated by Act_x%.

33. The method of claim 32, wherein the step of deriving the slope further comprises the steps of:

defining x% equal to about one percent; and defining c equal to about 0.25.

34. The method of claim 28, wherein the deriving step comprises the step of:

deriving the slope of the transfer function in accordance with the patient's regular exercise routine, whereby pacing therapy is administered such that during periods of exercise, the patient's heart rate is maintained at a predetermined target heart rate.

35. The method of claim 34, wherein:

the method further comprises the step of maintaining a running average of the sensor measurements; and the deriving step comprises the step of deriving the slope of the transfer function in accordance with the base pacing rate, the target heart rate, the running average, and the patient's profile of metabolic need as represented by the first histogram containing the selected sensor measurements stored over the predetermined period of time.

36. The method of claim 35, wherein the step of maintaining the running average comprises the step of:

digitally filtering the sensor measurements using a time constant of about 18 hours.

37. The method of claim 35, wherein:

the first histogram comprises a plurality of bins, each bin associated with a different sensor measurement; and the storing step comprises the step of incrementing a count associated with a particular bin when the sensor measurement to be stored in the first histogram corresponds to the particular bin.

38. The method of claim 37, wherein the deriving step comprises the step of:

deriving the slope of the transfer function in accordance with the relationship:

$$\text{Slope} = \frac{(\text{THR} - \text{BPR})}{(\text{Act\_Ex\%} - \text{Act\_Avg})},$$

wherein:

THR represents the target heart rate;

BPR represents the base pacing rate;

Act_Avg represents the running average of the sensor measurements;

Ex% represents a predetermined percentage of the predetermined period of time that the patient engages in exercise; and Act_Ex% represents a bin of the first histogram corresponding to a sensor measurement that is exceeded by no more than a percentage designated by Ex% of the sensor measurements stored as counts in the first histogram over the predetermined period of time.

39. The method of claim 28, further comprising the step of inhibiting derivation of the slope of the transfer function when the patient's level of metabolic need is below a threshold level over the predetermined period of time.

40. The method of claim 39, wherein:

the storing step comprises the step of storing sensor measurement deviation values as a second histogram over the predetermined period of time, the second histogram having a dominant mode and a mean; and the inhibiting step comprises the step of inhibiting derivation of the slope of the transfer function when the median is less than about 2.5 times the mode after the predetermined period of time has elapsed.

41. The method of claim 40, wherein the processing step comprises the step of:

deriving each sensor measurement deviation value by taking an absolute value of a difference between a current sensor measurement selected for storage in the first histogram and an earlier sensor measurement previously stored in the first histogram.

42. The method of claim 41, wherein the current sensor measurement is derived about 26 seconds after the earlier sensor measurement is derived.

43. The method of claim 28, wherein the deriving step is performed on a periodic basis.

44. The method of claim 28, wherein the predetermined period of time is about one week.

45. The method of claim 28, wherein the sensing step comprises the step of:

sensing levels of physical activity, the levels of physical activity being indicative of the levels of metabolic need.

46. A method of providing rate-responsive pacing therapy, comprising the steps of:

generating pacing pulses at a selectable rate;

sensing a patient's level of metabolic need;

selecting the rate at which pacing pulses are generated based on the sensed level of metabolic need and the corresponding heart rate defined by a transfer function that correlates metabolic need to heart rate, the transfer function comprising a slope that defines pacing rates between a minimum pacing rate and a maximum pacing rate;

automatically adjusting the slope of the transfer function in accordance with the level of metabolic need sensed over a predetermined period of time; and inhibiting automatic slope adjustment when the patient's level of metabolic need over the predetermined period of time is below a threshold level.

47. The method of claim 46, further comprising the steps of:

deriving sensor deviation values at predetermined intervals; and storing the sensor deviation values as a histogram over the predetermined period of time, the histogram having a dominant mode and a mean;

wherein the inhibiting step comprises inhibiting slope adjustment when the mean is less than about 2.5 times the mode after the predetermined period of time has elapsed.

48. The method of claim 47, wherein the deriving step comprises the step of:

deriving each sensor deviation value by taking an absolute value of a difference between a sensed current level of metabolic need and an earlier sensed level of metabolic need.

49. The method of claim 48, wherein the step of deriving each sensor deviation value comprises the steps of:

sensing the level of metabolic need about every 26 seconds; and defining the earlier sensed level of metabolic need as the level of metabolic need sensed about 26 seconds prior to the current level of metabolic need.

50. The method of claim 46, wherein further comprising:

defining the predetermined period of time equal to about one week.

51. The method of claim 46, wherein the sensing step comprises the step of:

sensing levels of physical activity, the levels of physical activity being indicative of the levels of metabolic need.

52. A rate-responsive pacemaker comprising:

pulse generating means for generating pacing pulses at a selectable rate;

physiological sensing means for sensing a patient's level of metabolic need;

rate selecting means for selecting the rate at which the pulse generating means generates pacing pulses by applying the sensed level of metabolic need to a transfer function that correlates metabolic need to heart rate, the transfer function comprising a slope that defines pacing rates between a minimum pacing rate and a maximum pacing rate, the minimum pacing rate and the maximum pacing rate have a minimum sensor threshold and a maximum sensor threshold associated therewith, respectively;

a memory for storing sensor measurements as a first histogram, the first histogram defining a frequency distribution of sensor measurements for a plurality of amplitudes, the first histogram further having a mode with a first amplitude value associated therewith corresponding to the patient's average metabolic need, and a second amplitude value at an upper end of the first histogram corresponding to an upper value for the patient's metabolic need;

means for adjusting the minimum sensor threshold to the first amplitude value; and means for adjusting the maximum sensor threshold to the second amplitude value.

\* \* \* \* \*